(12) United States Patent
Lusted

(10) Patent No.: US 10,517,536 B1
(45) Date of Patent: Dec. 31, 2019

(54) BIOMETRIC WEARABLE AND EDA METHOD FOR ACQUIRING BIOMARKERS IN PERSPIRATION

(71) Applicant: Senstream, Inc., San Francisco, CA (US)

(72) Inventor: Hugh Lusted, Oregon House, CA (US)

(73) Assignee: Senstream, Inc., San Francisco, CA (US)

( * ) Notice: Subject to any disclaimer, the term of this patent is extended or adjusted under 35 U.S.C. 154(b) by 0 days.

(21) Appl. No.: 16/368,683

(22) Filed: Mar. 28, 2019

Related U.S. Application Data

(60) Provisional application No. 62/648,997, filed on Mar. 28, 2018.

(51) Int. Cl.
| | |
|---|---|
| A61B 5/00 | (2006.01) |
| A61B 5/0205 | (2006.01) |
| A61B 5/145 | (2006.01) |
| A61B 5/024 | (2006.01) |
| A61B 5/053 | (2006.01) |

(52) U.S. Cl.
CPC .......... *A61B 5/6826* (2013.01); *A61B 5/0002* (2013.01); *A61B 5/0205* (2013.01); *A61B 5/4035* (2013.01); *A61B 5/7425* (2013.01); *A61B 5/02416* (2013.01); *A61B 5/0531* (2013.01); *A61B 5/14517* (2013.01); *A61B 2562/0209* (2013.01); *A61B 2562/063* (2013.01)

(58) Field of Classification Search
CPC . A61B 5/0002; A61B 5/0205; A61B 5/02416; A61B 5/0531; A61B 5/4035; A61B 5/6826; A61B 5/7425
USPC .......................................................... 600/301
See application file for complete search history.

(56) References Cited

U.S. PATENT DOCUMENTS

| | | | | |
|---|---|---|---|---|
| 5,964,701 A | * | 10/1999 | Asada ................ | A61B 5/02438 600/300 |
| 6,413,223 B1 | * | 7/2002 | Yang .................... | A61B 5/021 600/485 |
| 8,928,671 B2 | * | 1/2015 | Adler .................. | A61B 5/0022 345/473 |
| 9,311,825 B2 | * | 4/2016 | Lusted ................. | G09B 19/00 |
| 9,711,060 B1 | * | 7/2017 | Lusted ................. | G09B 19/00 |
| 10,139,859 B2 | * | 11/2018 | von Badinski ........ | G01P 15/00 |
| 2004/0117212 A1 | * | 6/2004 | Kong ................... | A61B 5/0205 705/2 |
| 2008/0214903 A1 | * | 9/2008 | Orbach ................. | A61B 5/486 600/301 |
| 2009/0318779 A1 | * | 12/2009 | Tran ..................... | A61B 5/0022 600/301 |

(Continued)

*Primary Examiner* — Christopher A Flory
(74) *Attorney, Agent, or Firm* — O'Banion & Ritchey LLP; John P. O'Banion

(57) ABSTRACT

A wearable biometric sensing ring apparatus for continuous heart rate and blood pressure monitoring having a ring housing for retention on a finger of a user, an electrodermal activity (EDA) sensor disposed within the housing so as to contact a location of the skin of the finger when the housing is retained on the finger, the EDA sensor configured for measuring changes in skin impedance indicative of SNS activation; a biometric sensor disposed within the housing in proximity to the EDA sensor so as to contact at or near the location of the skin of the finger. Application software is provided for assessing the physiological state of the user based on acquired EDA sensor data and biometric sensor data.

13 Claims, 13 Drawing Sheets

(56) References Cited

U.S. PATENT DOCUMENTS

| | | | | |
|---|---|---|---|---|
| 2010/0022852 A1* | 1/2010 | Westerink | A61B 5/0533 | 600/301 |
| 2012/0127157 A1* | 5/2012 | Adler | A61B 5/0022 | 345/419 |
| 2013/0095459 A1* | 4/2013 | Tran | A61B 5/6816 | 434/247 |
| 2013/0183646 A1* | 7/2013 | Lusted | G09B 19/00 | 434/236 |
| 2013/0317318 A1* | 11/2013 | Tartz | A61B 5/6843 | 600/301 |
| 2014/0275845 A1* | 9/2014 | Eagon | A61B 5/6826 | 600/301 |
| 2014/0316229 A1* | 10/2014 | Tognetti | A61B 5/0205 | 600/383 |
| 2014/0378859 A1* | 12/2014 | Taratorin | A61B 5/7214 | 600/547 |
| 2015/0182163 A1* | 7/2015 | Utter | A61B 5/0022 | 600/301 |
| 2015/0182164 A1* | 7/2015 | Utter, II | A61B 5/0022 | 600/301 |
| 2015/0186609 A1* | 7/2015 | Utter, II | A61B 5/0022 | 600/301 |
| 2015/0220109 A1* | 8/2015 | von Badinski | G01P 15/00 | 340/539.12 |
| 2015/0245777 A1* | 9/2015 | Della Torre | A61B 5/11 | 600/301 |
| 2015/0277559 A1* | 10/2015 | Vescovi | G06F 3/014 | 345/173 |
| 2016/0015313 A1* | 1/2016 | Sugarman | A61B 5/486 | 340/870.07 |
| 2016/0066845 A1* | 3/2016 | Kwon | A61B 5/6802 | 600/384 |
| 2017/0010663 A1* | 1/2017 | Tanaka | G06F 1/163 | |
| 2017/0086741 A1* | 3/2017 | Bly | A61B 5/6826 | |
| 2017/0127993 A1* | 5/2017 | Olivier | A61B 5/165 | |
| 2017/0135633 A1* | 5/2017 | Connor | A61B 5/4866 | |
| 2017/0181700 A1* | 6/2017 | Olivier | A61B 5/165 | |
| 2017/0196510 A1* | 7/2017 | Ouwerkerk | A61B 5/0531 | |
| 2017/0367614 A1* | 12/2017 | Zuckerman-Stark | A61B 5/6831 | |
| 2018/0035910 A1* | 2/2018 | Conchell Ano | A61B 5/0531 | |
| 2018/0042540 A1* | 2/2018 | Kinnunen | A61B 5/16 | |
| 2018/0103868 A1* | 4/2018 | Seko | A61B 5/0533 | |
| 2018/0120892 A1* | 5/2018 | von Badinski | G06F 3/1423 | |
| 2018/0177418 A1* | 6/2018 | Yu | A61B 5/681 | |
| 2018/0279953 A1* | 10/2018 | Wang | A61B 5/6831 | |
| 2018/0317770 A1* | 11/2018 | Ortega | A61B 5/6824 | |
| 2018/0360373 A1* | 12/2018 | Aarts | A61B 5/0059 | |

* cited by examiner

BIOMETRIC WEARABLE AND EDA METHOD FOR ACQUIRING BIOMARKERS IN PERSPIRATION

CROSS-REFERENCE TO RELATED APPLICATIONS

This application claims priority to, and the benefit of, U.S. provisional patent application Ser. No. 62/648,997 filed on Mar. 28, 2018, incorporated herein by reference in its entirety.

This application is related to U.S. patent application Ser. No. 16/026,450 filed on Jul. 3, 2018, incorporated herein by reference in its entirety, which claims priority to, and the benefit of, U.S. provisional patent application Ser. No. 62/528,336 filed on Jul. 3, 2017, incorporated herein by reference in its entirety.

NOTICE OF MATERIAL SUBJECT TO COPYRIGHT PROTECTION

A portion of the material in this patent document may be subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to biofeedback devices, and more particularly to biometric wearables for short, medium, and long-term data acquisition and analysis applications.

2. Background Discussion

Electronic physiological monitoring equipment has long been available in various forms. Typically, these devices are configured for fulfilling a very specific and narrow role. For example, the electrocardiograph (ECG) is used to record the pattern of depolarization of the heart muscles as blood is pumped to the lungs for oxygenation and then out to all parts of the body. The ECG produces a pattern of electrical waves that are of diagnostic importance as related to heart function.

Another specific device is the photoplethysmograph (PPG), which is well known in hospitals for quick assessment of heart rate based on sensing at the fingertip. A third specific device is used to measure electrodermal activity (EDA) which is a skin impendence measurement that indicates sympathetic nervous system (SNS) activation. Another example is a self-contained "biosensor" that can measure chemical biomarkers in perspiration. However, these devices are generally directed to specific purposes in short term testing and not generally applicable for long term use and interaction with a user. In addition, the data from these separate devices are not combined to enable multichannel calculations and analyses.

Biosensor analysis of perspiration has been shown to be an effective way to assay certain chemicals in the bloodstream that are important for human health—such as glucose, lactic acid, cortisol, and several others. Wearable biosensors have been described by various research groups, and there is a tacit assumption that perspiration is continuously available for analysis beneath the wearable enclosure. In actuality, perspiration is generally not available on the skin unless the user is physically active for a prolonged period. One research group has addressed the issue of lack of perspiration by artificially stimulating the eccrine glands using a neurotransmitter that is pushed through the skin using iontophoresis. This then allows a biosensor to do a glucose assay. Another method uses iontophoresis to draw interstitial tissue fluid out of the skin so a biosensor can test for certain biomarkers. There are several drawbacks with these stimulation methods including (a) user discomfort with prolonged wear, (b) eccrine gland habituation over time, (c) long latency to yield sufficient fluid, and (d) greatly reduced battery life due to requirements of electrical current injection into the skin.

BRIEF SUMMARY

Accordingly, the present disclosure overcomes the limitations of these short-term discrete testing devices, while providing additional advantages.

The technology presented provides for placement of one or more biometric sensors on the finger, with the combination of sensor data allowing a determination of accurate assessments of the physiological state of the user within applications executing on a mobile device. A multichannel finger sensor system has been previously described in U.S. Pat. No. 9,311,825 which is incorporated herein by reference in its entirety.

Advantageously, various embodiments of the technology described herein may incorporate one or more of the following elements: (a) an EDA sensor that can produce both electrodermal response (EDR) and electrodermal level (EDL) data, (b) a biosensor whose data can be combined and correlated with the EDA sensor to assess the physiological state of the user, (c) wireless data connection and processing hardware (e.g. Bluetooth Low Energy (BLE) integrated processor), and (d) inclusion of sufficient capacity energy storage (e.g., battery) to allow a user to wear the ring for extended periods of time (e.g., all day) which enables long term biometric data collection. This continuous data collection capability provides a new window on monitoring chemical biomarkers and accompanying SNS activity in real life situations.

The system and methods of the present disclosure do not require use current injection or artificial stimulation of the eccrine glands, and incorporate a method for perspiration sampling that makes use of the electrodermal response (EDR). By definition, the peak of the EDR wave is the electrical signature of the maximal perspiration secretion from the eccrine glands. Thus, the peak of the EDR is here used to activate the chemical assay process. Biosensors are specific for the assay of certain biomarkers, and the system disclosed here is intended to function with all self-contained biosensors that use an electrical circuit for chemical analysis.

The technology can be implemented with dedicated hardware, or for the sake of simplicity of implementation, may be executed using existing electronic devices. By way of example and not limitation, instructions of an application program (or programs) may be loaded for execution on a general-purpose electronic processing device, such as a mobile device (e.g., smart phone, tablet, notepad, netbook, laptop, etc.). In at least one implementation, no additional hardware or hardware changes are required on the mobile device side. Thus, a user need only obtain the ECG, PPG, EDA sensor device or biosensor device for streaming data to their mobile device, and the desired application to execute from that mobile device.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

1. Biosensor Hardware Configuration

The continuous wearing biometric sensor of the present disclosure is configured to incorporate multiple sensor types into a package wearable on any finger of a user's hand.

Figure 1:
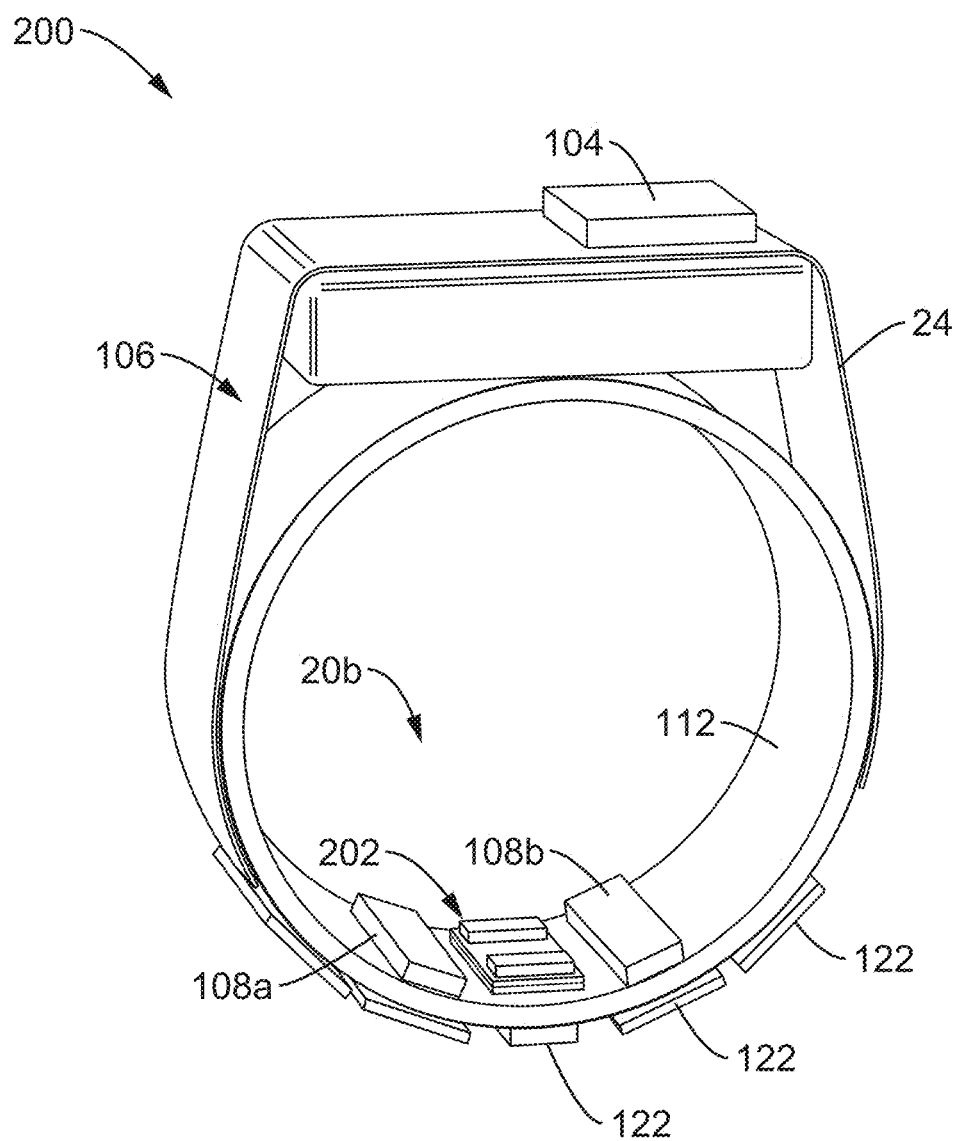
FIG. 1 is a perspective image of an EDA and biosensor capable ring with the biosensor module between the EDA electrodes according to an embodiment of the technology of this disclosure.

FIG. 1 shows a schematic diagram of an EDA triggered biosensor ring system 200 comprising an EDA sensor 36 for measuring user SNS activation, having a pair of EDA electrodes 108a and 108b configured to contact the palm side of the finger where there is the greatest density of eccrine sweat glands that respond to SNS activation, and a biosensor 202 that is located between the two EDA electrodes E1 and E2 in FIG. 2. In the embodiment shown in FIG. 1, the biosensor 202 is shown as a single module. However, other configurations may be employed.

Figure 2A:
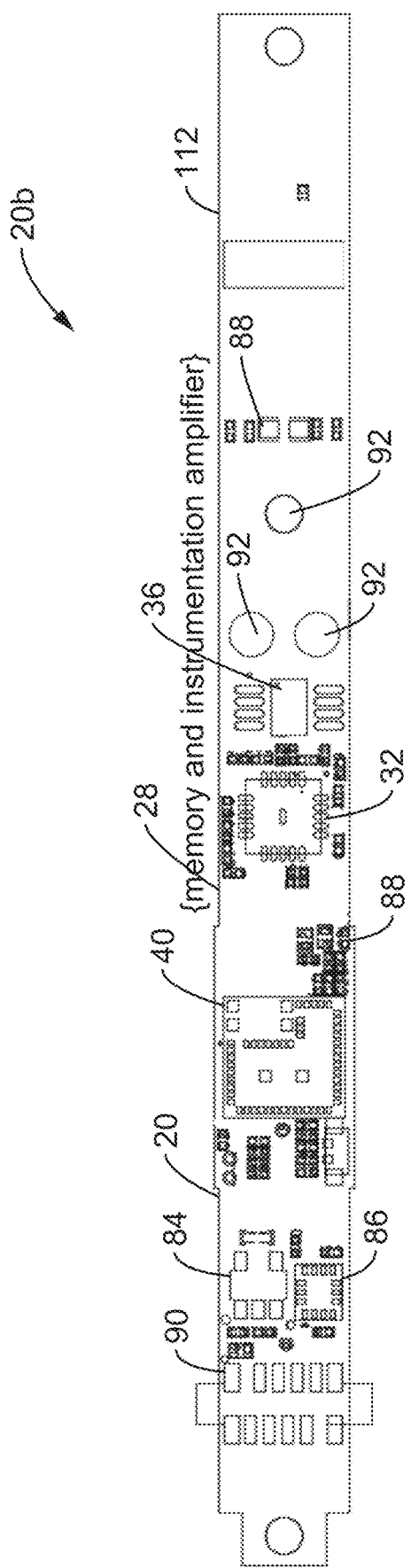
FIG. 2A and FIG. 2B are schematic diagrams of top and bottom views (respectively) of a flex board layout for use with and fit inside the ring configuration of FIG. 1.
Figure 2B:
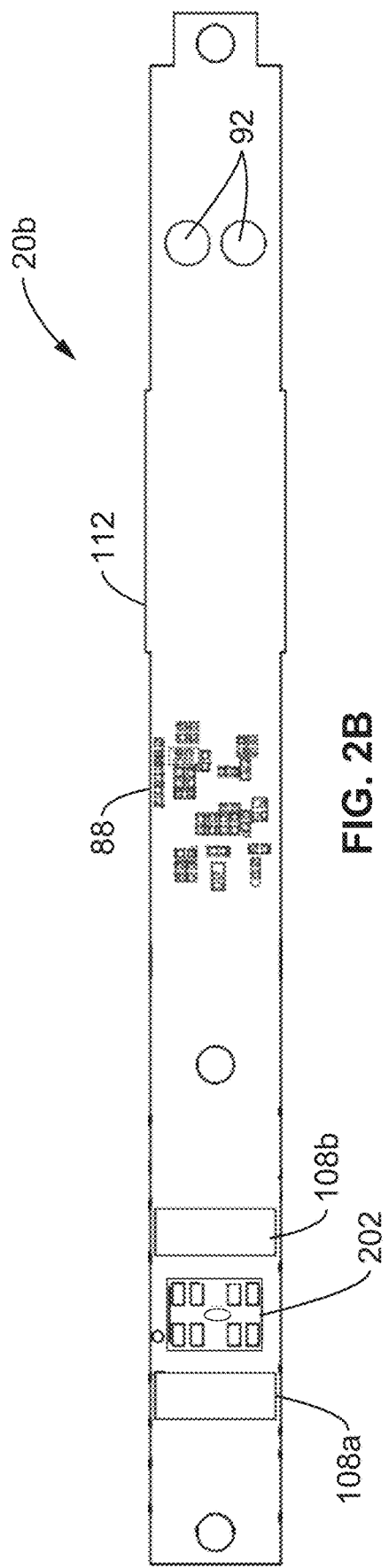

Biosensor ring system 200 comprises ring enclosure 102 (the outer part of the ring enclosure 102 is removed in FIG. 1 for visibility) with sensing and logic components disposed on a flex board 20b disposed within enclosure 102. A BLE module 104 and battery 24 are disposed in the top area of the ring 200. The BLE may also be on the flex board 20b (as detailed in FIG. 2A and FIG. 2B showing BLE processor 40). A pair of EDA electrodes (108a, 108b) are shown straddling opposite sides of biosensor module 202 on the bottom interior sensing surface of the aperture of the ring 200 defined by the substrate 112 of flex board 20b. Additional circuit component chips 122 may be positioned on the opposite or outer side of the flex board 20b (in between).

It should be appreciated that the processor, op amps, memory, BLE module, battery, and passive components (all not shown) are all preferably distributed along the board 20b to allow flex spaces between the components. It is also preferable that the sensor surfaces be mounted on the bottom interior of the ring to provide reliable contact with the skin of the user's finger. Ring enclosure 102 may also comprise an antenna (e.g. Bluetooth antenna or the like) comprising a trace at the upper location of the ring 100.

Referring to FIG. 2A and FIG. 2B, the interior sensing surface of flex board 20b (shown in FIG. 2B) comprises EDA electrodes 108a, 108b (E1 and E2) that straddle opposite sides of biosensor module 202 on the flexible substrate 112, along with passive components 88 and battery charger contacts 92. On the opposite side (FIG. 2A), the flex board 20b comprises processors, logic, memory and other various components disposed between flex areas 28, including but not limited to memory and instrumentation amplifiers 32 and 36 (e.g. for the EDA sensor or other sensors), a Bluetooth Low Energy (BLE) chip 40, 3V voltage regulator 84, integrated motion unit (IMU) 86, and a series of programming connector contacts 90 is included for CPU boot loading and functions testing. Passive component sections 88 may comprise a series of passive components, where each horizontal pair of contacts comprises a surface mount for a resistor or capacitor.

It is appreciated that the flex board 20b may comprise any number of shapes and sizes. For example, a wearable patch configuration (not shown) may incorporate a flex board that is less rectangular based on the desired location of adhesion.

While incorporating both of the EDA sensors and biosensors is preferred, it should be appreciated, however, that the biometric sensor ring of the present disclosure may include more sensors (e.g. ECG sensors, PPG sensor, accelerometer, and thermistor or the like) without departing from the teachings of the presented technology.

It is preferred that the EDA and biosensor surface be mounted on the bottom interior of the ring to provide reliable contact with the skin of the user's finger. The design allows for a comfortable fit and also minimizes motion artifacts generated by skin/sensor movement.

Figure 3:
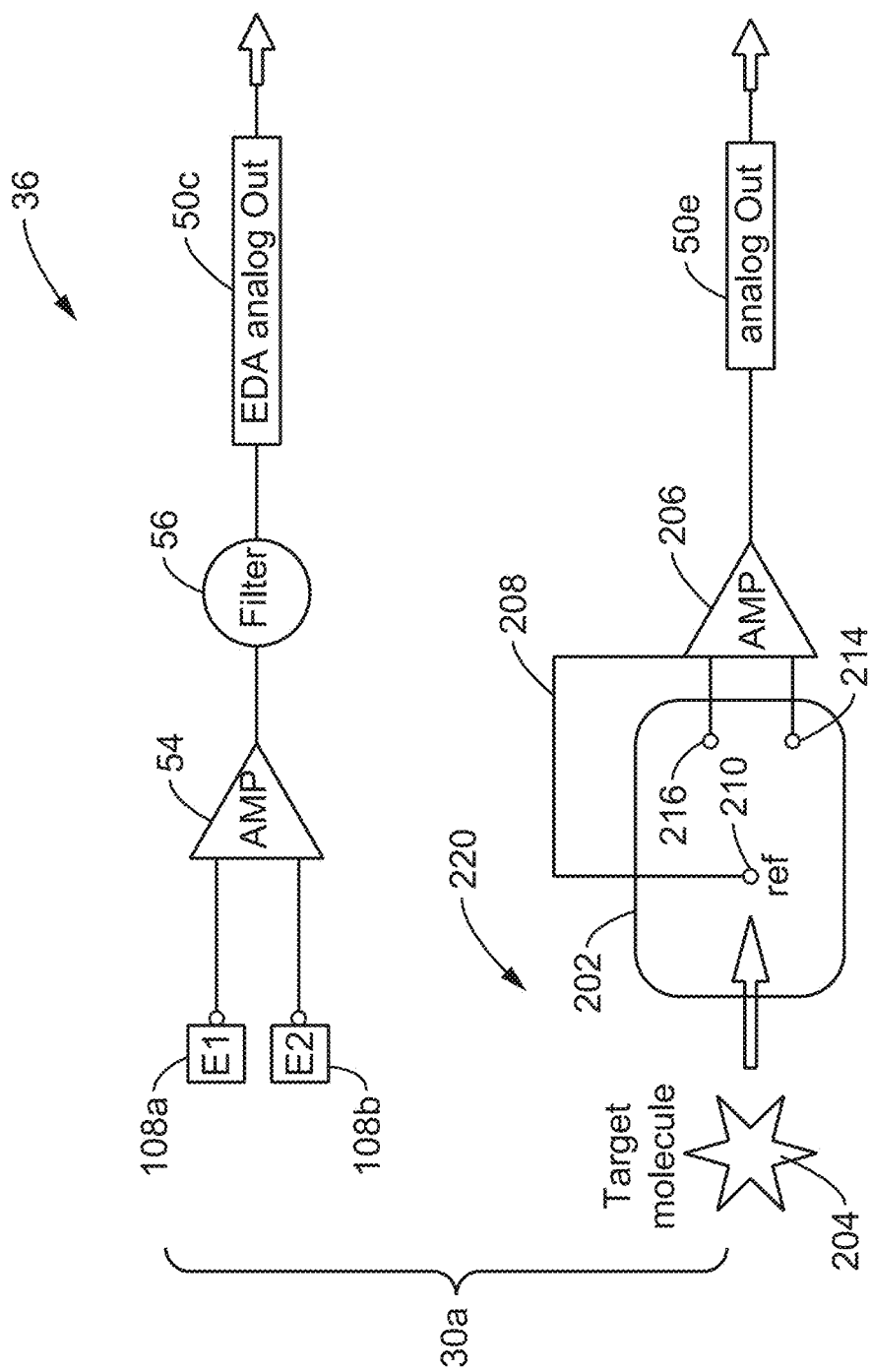
FIG. 3 shows sensor circuit schematic diagrams for the EDA and biosensor inputs according to embodiments of the technology of this disclosure.

FIG. 3 is a schematic diagram of sensor circuit data capture and processing architecture 30a of the various sensors on the flex board 20b. An EDA (electrodermal activity) sensor 36 is provided to measure an EDA signal generated from electrodes E1 and E2 (18a and 18b) that register changes in skin resistance. The signals are amplified with an instrumentation amplifier 54 and low pass filter 56 to minimize 60 Hz environmental electrical noise that are integrated on the EDA sensor 36 (e.g. INA156 instrumentation amp). In a preferred embodiment, the EDA electrodes 18a and 18b contact the palmar side of the finger where there is the greatest density of eccrine sweat glands that respond to SNS activation. The analog EDA output signal 50c inputs to an A/D input 62c on the integrated processor 40 as shown in FIG. 4.

Figure 4:
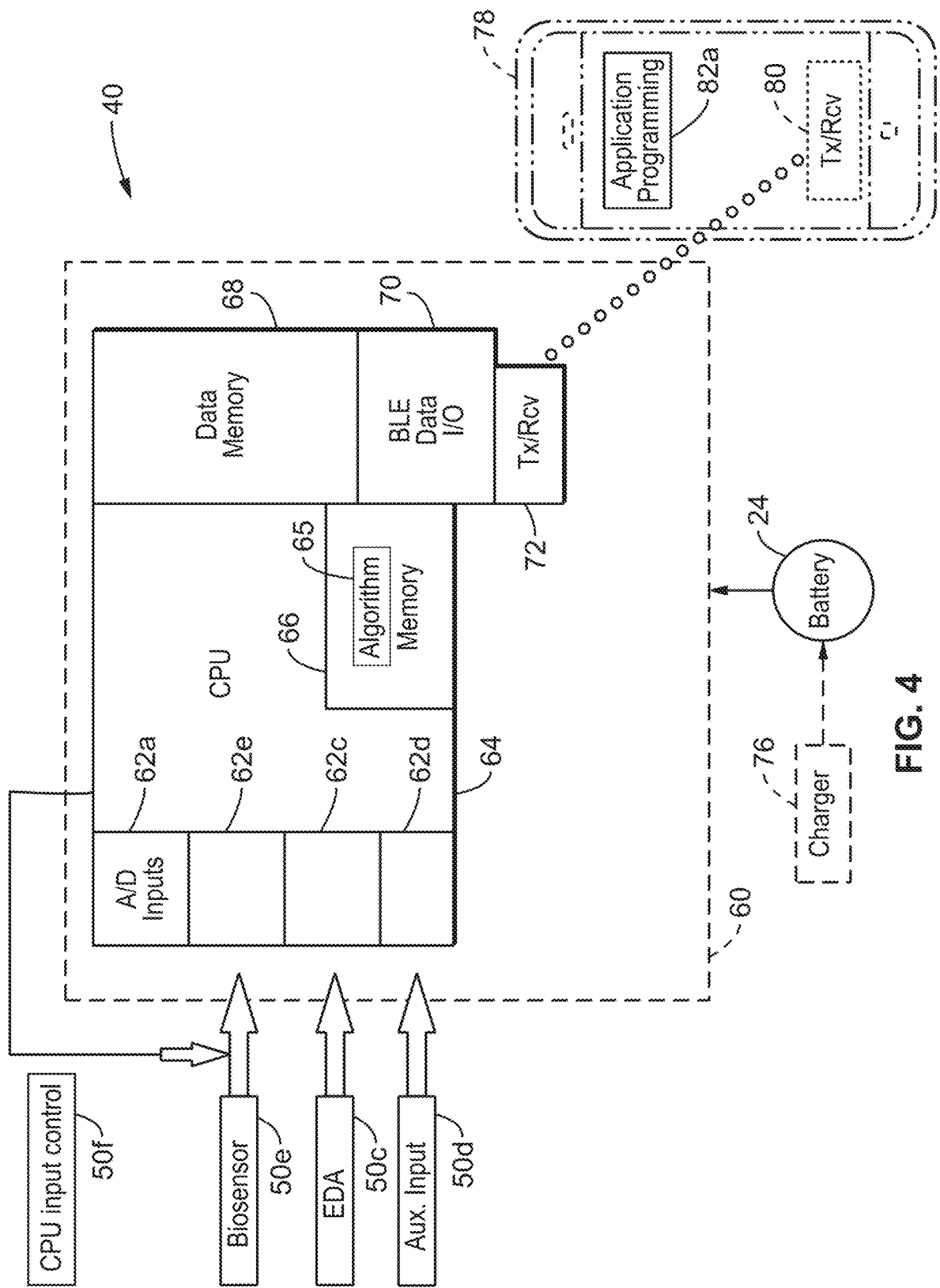
FIG. 4 is a schematic diagram a biometric ring circuit architecture according to an embodiment of the technology of this disclosure.
Figure 5:
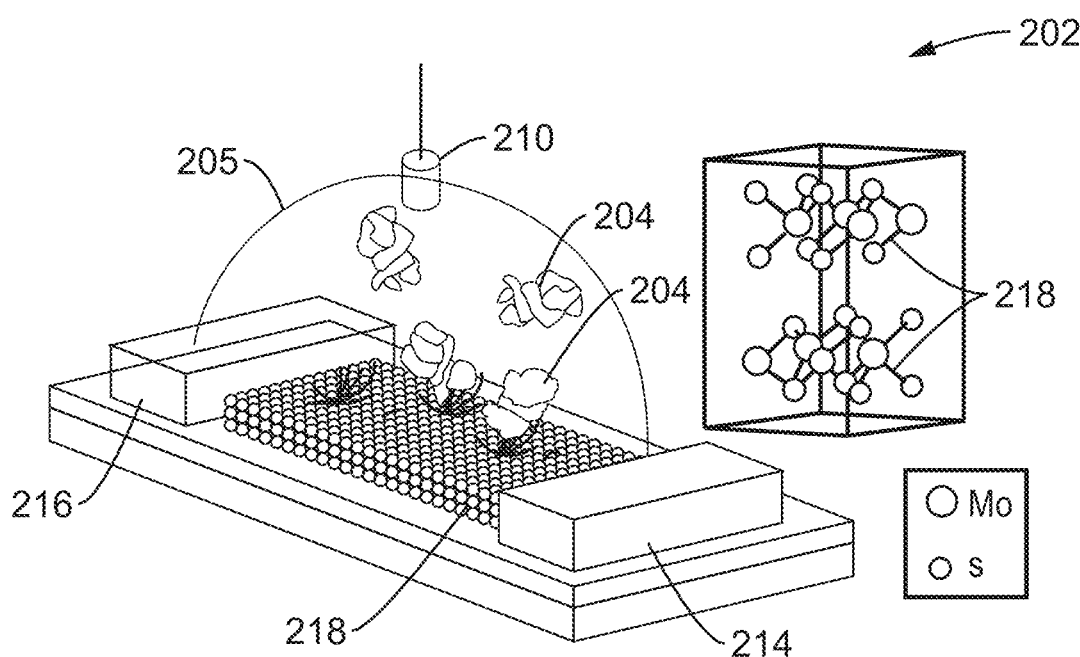
FIG. 5 is a schematic diagram of an exemplary biosensor circuit configuration and the elements used to create a field effect transistor, wherein a target molecule can modulate the current output of the sensor.

Sensor circuit data capture and processing architecture 30a also includes a biosensor circuit 220 that is exemplified by an integrated FET (field effect transistor) design, wherein a target molecule 204 interacts with reagents or enzymes in the reaction surface of biosensor 202 between source 216 and drain 214, which modulates the device current (see FIG. 5). Reference or bias signal 208 may be applied to reference electrode 210 to bias an electrolyte at the region. The received signal from surface 202 is modified by instrumentation amplifier 206, and the output biosensor analog signal 50e is input to a corresponding A/D 62e on the integrated processor 40 as shown in FIG. 4.

Referring to FIG. 4, the integrated BLE processor 40 the sensor outputs 50a, 50c 50d and 50e are received at respective inputs 62a, 62c, 62d and 62e. An auxiliary A/D input 62d may also be included to receive auxiliary input 50d from one or more auxiliary devices, e.g. 3D motion data, temperature data, or chemical assay data from an accelerometer, thermistor, or nanotube array (all not shown) respectively.

In input signals are then preferably conditioned, typically including amplification and/or filtering, followed by conversion to a digital signal, such as by an analog-to-digital converter, prior to receipt by a processing unit 64 (e.g., CPU, microprocessor, microcontroller, DSP, or one or more electronic devices configured to process the sensor signals). Instructions 65 for execution by the processor (or processors) and data, are stored in one or more memories (e.g. algorithm memory 66). The CPU 64 runs signal processing methods for analyzing features of the multi-sensor data stream. The CPU 64 may also generate an input control signal 50 to the sensors. Results of signal processing and raw itself can be stored in the data memory 68. The abovementioned components, along with BLE data I/O module 70 and wireless transmission/receiver module 72 may all be integrated on one logic device 60 (e.g. BCM121 integrated BLE processor).

It will also be appreciated that the computer readable media (memory 66 storing algorithm instructions 65) in both the biometric sensor ring 200 and external applications (e.g. application programming 82a in portable device 78) to which it communicates, are computation systems with memory that are "non-transitory", i.e. they may comprise any and all forms of computer-readable media, with the sole exception being a transitory, propagating signal. Accordingly, the disclosed technology may comprise any form of computer-readable media, including those which are random access (e.g., RAM), require periodic refreshing (e.g., DRAM), those that degrade over time (e.g., EEPROMS, disk media), or that store data for only short periods of time and/or only in the presence of power, with the only limitation being that the term "computer readable media" is not applicable to an electronic signal which is transitory.

By way of example and not limitation, at least one embodiment of the instruction programming 65 (e.g., firmware) is configured for scanning the EDA and biosensor channels at different frequencies with voltage level data streamed to application programming, which may also execute on a remote device, preferably a smart phone. In one embodiment the BLE module 40 contains the firmware memory, although various other memory configurations can be utilized without departing from the present disclosure. Embodiments of the application programming for smart phones may be implemented for iOS, Android or other operating systems. This application 82a, which executes from the smart phone 78 can perform a wide variety of biosensing data collection, analysis, and display functions. For example, one embodiment of firmware records a time stamp, records EDA level every 20 msec and records the biosensor output every 200 msec, determines, records, and displays the sensor outputs on the app device screen.

The input gains are adjustable depending on the level of the input sensor signal, which can vary more than a factor of 100 (100 uV for EDA versus 10 mV for the biomarker—depending on the type of sensor circuit used), so the input stage is shown configured to scaling for these large differences. The analog signals are converted to digital signals in the processor A/D (analog to digital converter). The sampling rate of each channel can be independently set depending on the bandwidth of the input signal.

A wireless communication protocol is also supported as exemplified with BlueTooth Low Energy (BLE) device 70 comprising or coupled to a transmitter/receiver 72 shown for wirelessly communicating with Tx/Rcv 80 of another electronic device 78 (e.g. smart phone or the like), which can allow for controlling device operation, registering collected sensor data, analyzing collected data, displaying collected data or analyzed data, or any combination thereof. It is appreciated that the BLE module 70 may contain the radio (Tx/Rcv) 72, wherein there is no need for the separate Tx/Rcv 72 shown in FIG. 4. Data can be uploaded to an external network at any time, such as via the exemplified BLE I/O module 70. The BLE module 70 utilized in the example embodiment may contain its own processor and memory and can be configured for different types of network protocols aside from the BlueTooth protocol. New signal processing algorithms 65 can be downloaded to program memory in the CPU 64 via the BLE module 70. In one implementation, the BLE module 70 may contain the A/D inputs, processor, memory (e.g., instruction programming, firmware), transmit/receive radio, and antenna.

A self-contained power source, exemplified as a battery 24, is shown for powering the ring sensing device 10, and is shown with an optional charger 76, thus allowing the user to be move about during the course of their normal activities.

Biosensor 220 may be of various types and designed to assay specific target molecules. FIG. 5 is a schematic diagram of an exemplary biosensor circuit configuration 202 in the form of a $MoS_2$ field effect transistor, wherein target molecules 204 interact with reagents or enzymes in the reaction surface 218 of biosensor 202 between source 216 and drain 214 to modulate the current output of the sensor 202 The one component that biosensors have in common is a reaction surface 218 for initiating chemical analysis of a sample of sweat. The receptor molecules of the reaction surface 218 are preferably functionalized with receptors for specifically capturing target molecules. An electrolyte gate is formed may via reference electrode 210, which is used to bias electrolyte 205 at the region and charge the target biomolecules to induce the gating effect.

While the $MoS_2$ FET 202 shown in FIG. 5 is particularly useful for the ring system 200, other example biosensor devices available and known in the art may be implemented potentially fit on the ring inner surface.

2. Sweat Sampling Process Using EDA

The sweat glands are generally innervated by SNS fibers that stimulate the production and release of sweat. There is no parasympathetic nervous system (PNS) innervation, and when SNS activation stops the bead of sweat at the surface of the skin is generally withdrawn into the gland's tubule.

Figure 6:
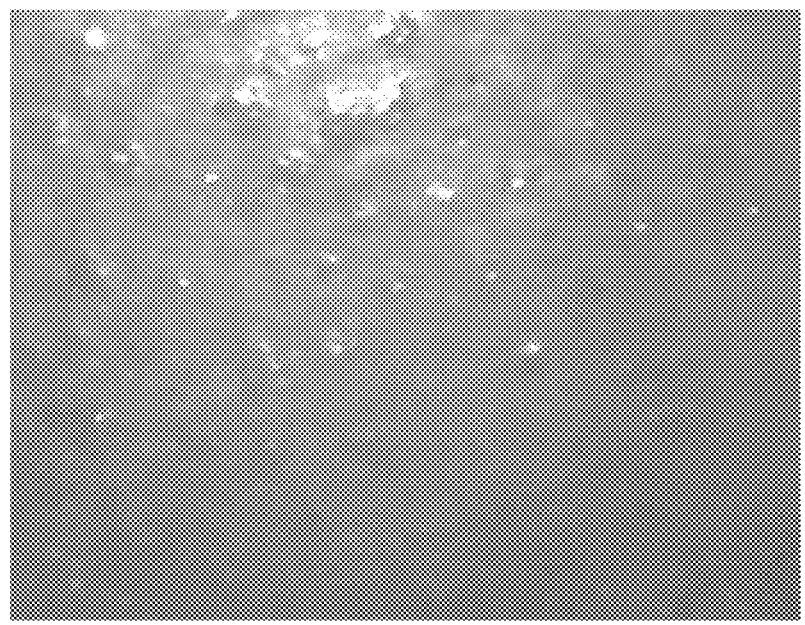
FIG. 6 is a photograph (magnification 20x) showing dilated finger eccrine glands releasing beads of perspiration.
Figure 7:
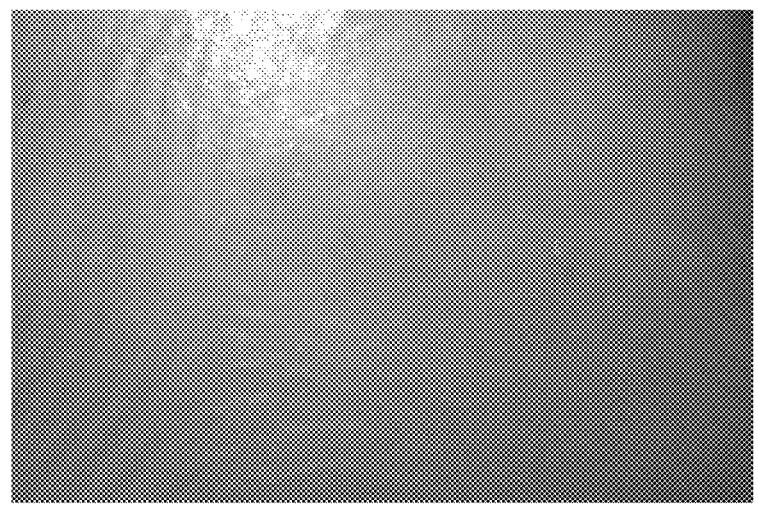
FIG. 7 is a photograph (magnification 20x) showing retracted finger eccrine glands with perspiration resorbed.

Emotional activation of the SNS produces eccrine gland sweating in the fingers and hands and produces an electrical signature from an EDA sensor. It is possible to visualize the activated eccrine glands using a microscope as shown in FIG. 6. The sweat beads can be clearly seen on the surface of the skin as they emerge from the sweat pores. When SNS stimulation subsides the glands close and withdraw the sweat secretions, as shown in FIG. 7. These photomicrographs are frames from a video of an index finger where the eccrine population can be seen to produce sweat beads in response to an inhalation by the test subject.

Figure 8:
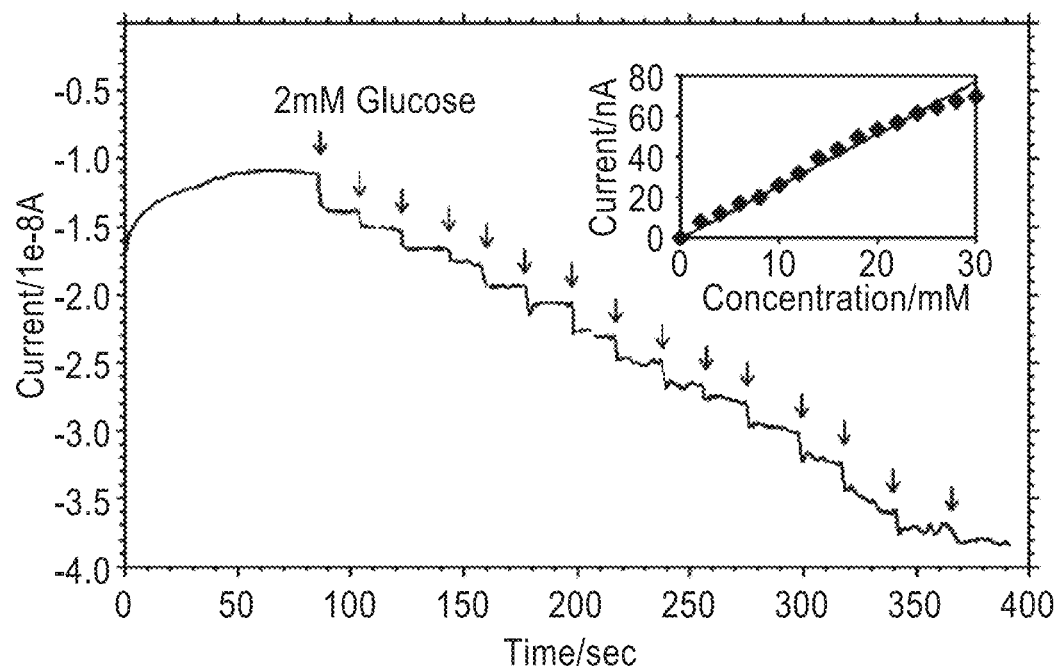
FIG. 8 is a plot of the current output from the biosensor of FIG. 5 as the concentration of glucose is incrementally changed.

FIG. 8 shows an example plot of the current output from the biosensor 202 as the target molecule concentration is increased in increments. The biosensor output 52e is an analog input 62e to the wearable's processor 40, as shown in FIG. 4.

Figure 9:
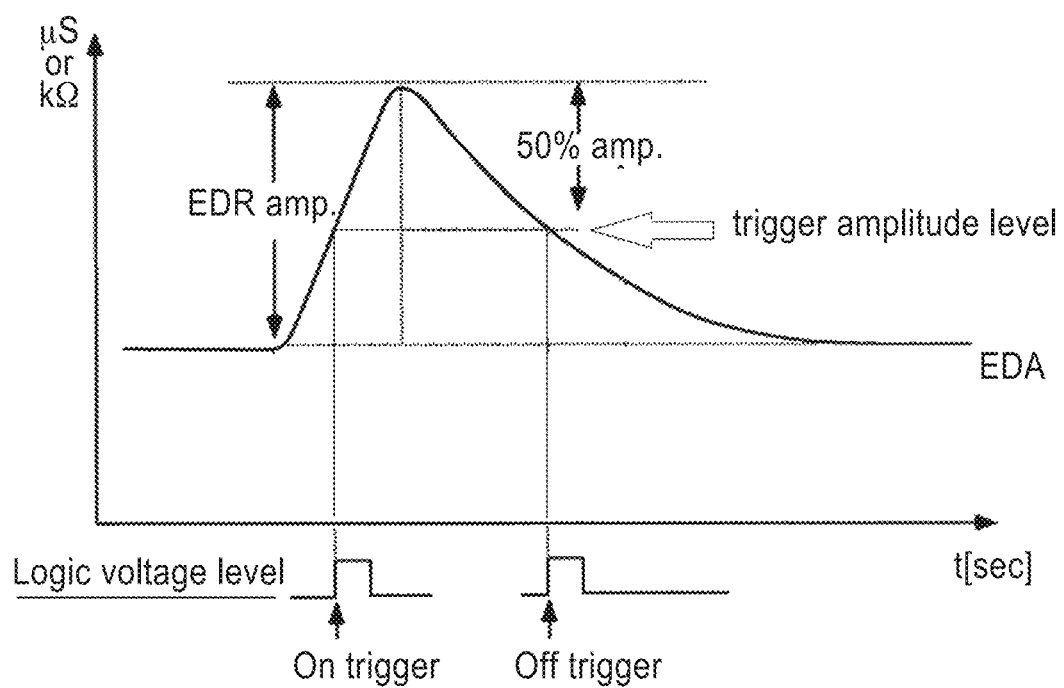
FIG. 9 is a plot showing an EDR response used to trigger a logic circuit based on threshold detection at a specified EDR voltage level.

In a preferred embodiment, the process of acquiring a biomarker assay is activated by the EDA response acquired from EDA sensor circuitry 36. The biosensor 202 is located adjacent to the EDA electrodes 108a/108b so both sensors are in the same area of eccrine gland density on the finger. When the EDR amplitude reaches a pre-set threshold, the application software 65 as executed by the processor 40 activates the biosensor circuit 220 to acquire data. FIG. 9 shows an example EDR voltage threshold set at 50% of the maximum EDR amplitude. In one embodiment, his threshold is set by a Schmitt trigger type algorithm that outputs an "on" signal when the trigger level is exceeded. In this example, when the EDR amplitude drops back below the threshold level, an "off" signal is generated. The trigger parameters are software adjustable, so any EDR amplitude level can be set, and the trigger algorithm can activate the biosensor once per EDR or count multiple EDRs before activating the biosensor. This programmable feature is important for biosensors that perform single-use assays—and then need to be reloaded with new reaction components (e.g. immunoassay of cortisol).

3. Biometric Signal Processing

The biometric ring 200 is configured to send sensor data to a mobile device 78, such as through the BLE interface 40, to be decoded in the mobile device application software 82a to provide one or more of the following functionalities/outputs: (a) display information in a raw data form (e.g., graphing routine); (b) analyze (process) the information and display average values, time related values, threshold related values, emotional state charts/plots/indicators; (c) displaying animations to depict the raw and/or analyzed sensor information; (d) utilize the raw and/or analyzed data within an application that uses contextual inputs and performs further analyses such performed by a machine learning (ML) network that can recognize patterns in large data sets that may not be apparent in simple data displays (also, application 82a may also take inputs from keyboards, pointing devices, mobile device motion sensing, mobile device position (i.e., GPS), etc.).

3.1. Biosensor Activation Process

Figure 10:
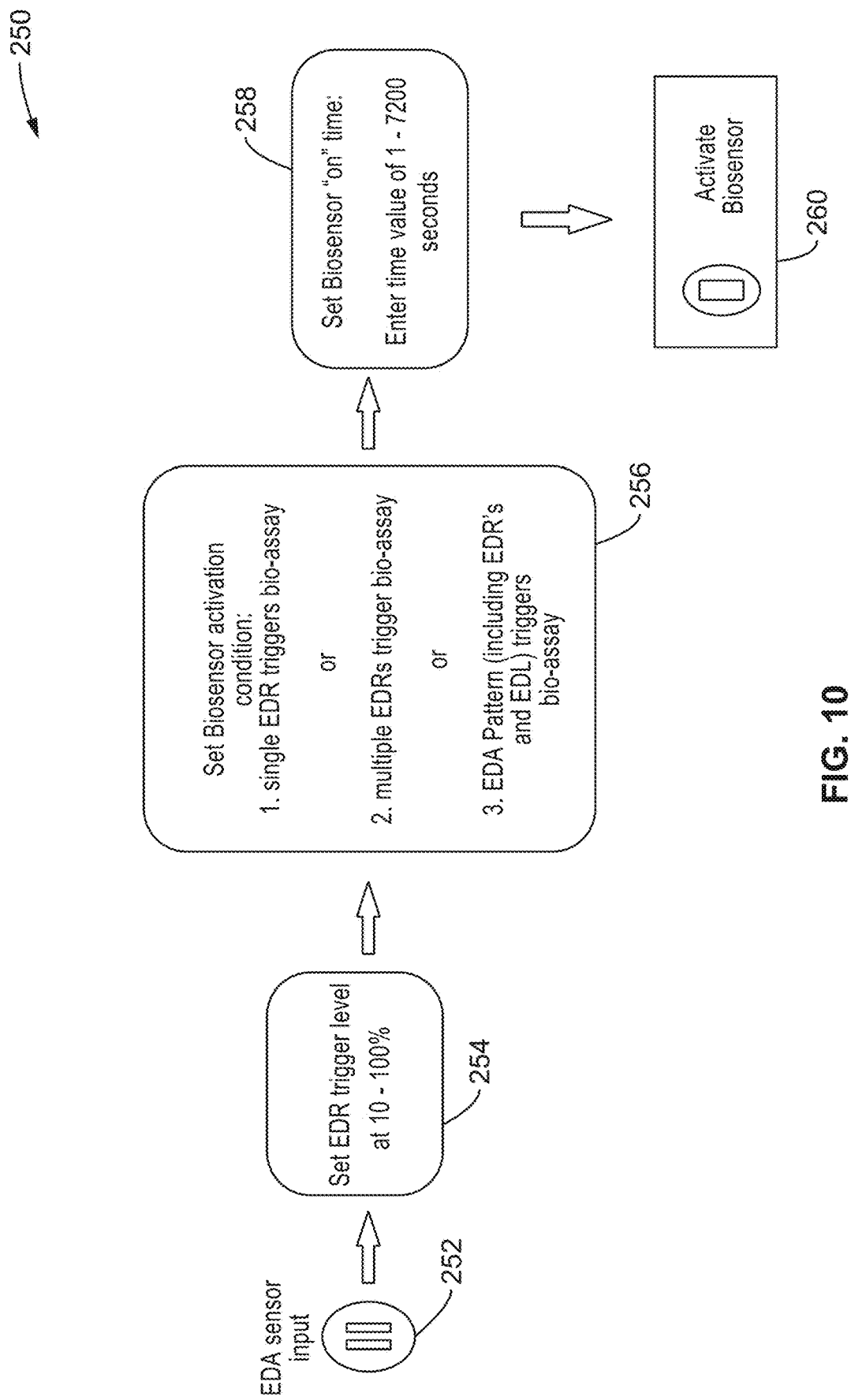
FIG. 10 shows a schematic flow diagram of a biosensor activation process using EDA input in accordance with a method of the technology of this disclosure.

FIG. 10 shows a schematic flow diagram of a biosensor 202 activation process 250 using EDA input 252 in accordance with the technology of this disclosure. The analysis of EDA data may be performed on the mobile device application software 82a or via application programming 65 and processor 40 on the ring 200, and allows the user to set various parameters to determine the timing of activation of the biosensor and thus control the bio-assay process for different conditions of use.

Figure 12:
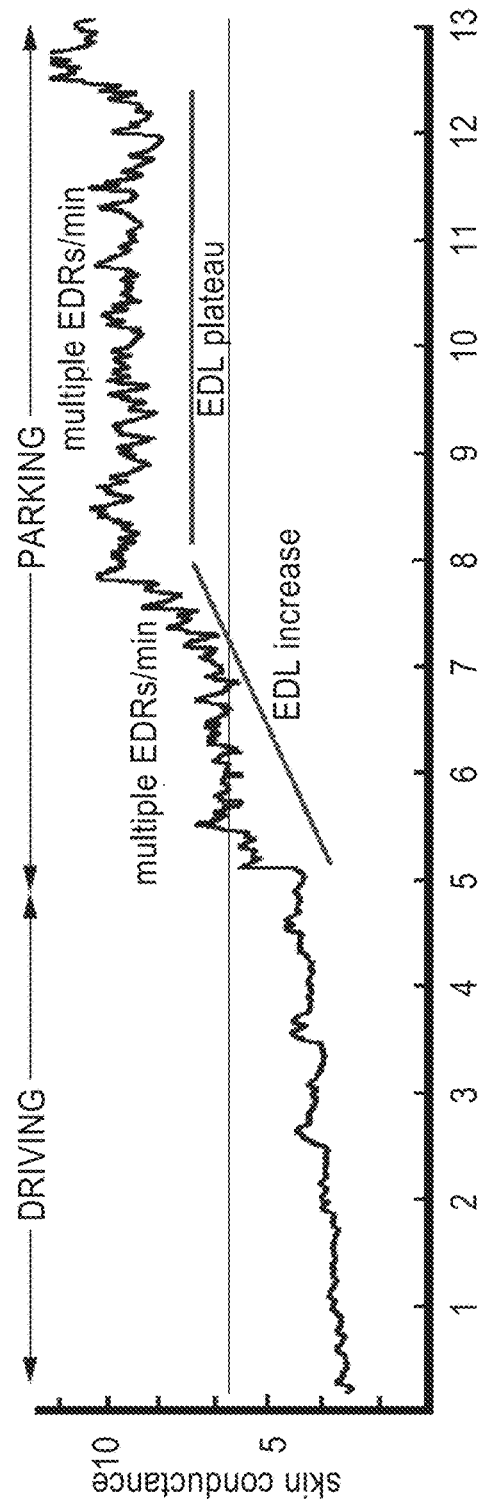
FIG. 12 shows a plot of an EDA activation pattern while a user is experiencing changing environments/activities of driving and parking, exemplifying the distinction between EDR activations per minute and the changing EDL baseline.

As shown in FIG. 10, the user can first set the trigger amplitude at block 254 for an individual EDR as diagramed in FIG. 9. Next, at block 256 the activation condition can be selected as: 1) a single EDR that activates the biosensor 202 and initiate a bio-assay; 2) multiple EDRs that activate the biosensor 202; and 3) an EDA pattern can be programmed and selected to activate the sensor 202. The EDA pattern can include both EDR and EDL data elements. An example of both EDR and EDL being significant is shown in FIG. 12 wherein the EDL baseline increases over time concomitant with multiple EDR activations.

In addition to the activation condition, the user can select the "on" time for the sensor to perform its bio-assay at block 258, after which the biosensor will stop or turn "off" acquisition. The typical range of on times is from 1 to 7200 (2 hours) seconds depending on the use case and the type of biomarker being assayed. After the use case conditions are set, the app will activate the biosensor at step 260 when the criteria are met. In an alternative configuration, an "off" trigger may be set at a percentage of amplitude level (see FIG. 9).

3.2. Intentional Biosensor Activation by EDR

Figure 11:
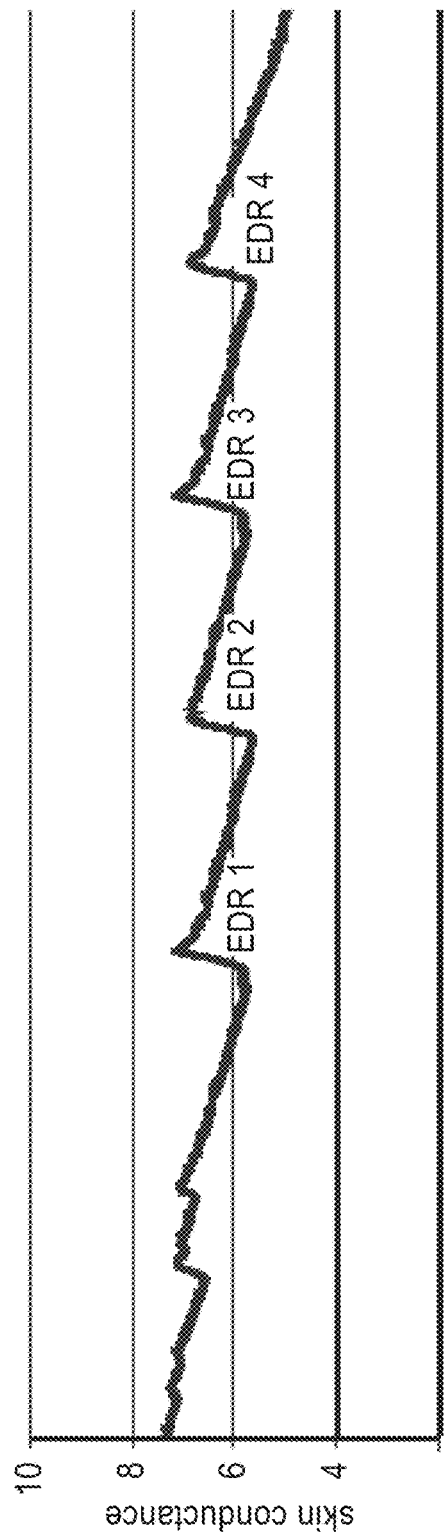
FIG. 11 is a plot showing a series of EDRs produced intentionally by user inhalations spaced 10 seconds apart.

Given the activation interface between the biosensor 202 and the EDR detection circuit 36 shown in FIG. 8 and the activation process 250 shown in FIG. 10, the method of biosensor activation has a behavioral component that allows users to initiate the biomarker analysis process. For most users an inhalation triggers a minor SNS activation that produces an EDR wave, and a deep inhalation produces a sizable EDR. FIG. 11 shows example EDRs produced by inhalation. Depending on the type of biosensor 202, this form of activation can be employed at any time by the user. Some biosensors have a long chemical reaction latency, so the system can be programmed to use an EDR activation only after a specific time has elapsed since the previous sample. An example situation wherein a user would like to trigger a biomarker assay may be just after a meal and a glucose measurement would be useful for tracking insulin activity. Another example would be tracking stress responses during or after confrontational situations. The user could activate the biosensor to assay the cortisol level in circulation.

3.3. Intentional Biosensor Activation with Multiple EDRs

In a similar manner to that described in Section 3.2, the user could select an option in the mobile app 82A that would enable activation of the biosensor 202 with a pre-set number of inhalations. For instance, two or more inhalations could be programmed to activate the biomarker assay process—as exemplified in the four-inhalation induced EDRs in FIG. 11. This would be useful for users who have higher SNS sensitivity and have many small EDRs (that may trigger the biosensor) in normal situations—and who want to activate the biosensor only in particular situations. An example would be a user who has a particular phobia and wants to activate a cortisol assay in a normal situation to see if the adrenals are over active.

3.4. Autonomic Biosensor Activation by EDA

In some situations, there is a pattern of EDA activation (both EDR and EDL) that is determined by the user's emotional state. There may be a pattern of general SNS activation that is extreme, of which the user may have no awareness. In this situation, pattern recognition software can be employed to activate the biosensor 202 at specific intervals to track metabolic activity through the course of user activities. This type of metabolic tracking is useful for determining the how the user is dealing with long term stress, for instance. At present, a single blood test done periodically is the only way a doctor can track someone's hormonal response to stress.

FIG. 12 shows an example EDA activation pattern that was recorded as the user was looking for parking in a busy city. The stress pattern shows multiple EDR activations per minute followed by an increase in the EDL baseline. Extreme frustration is indicated when the EDL plateaus and there are still multiple EDRs per minute occurring on top of the elevated baseline.

Figure 13:
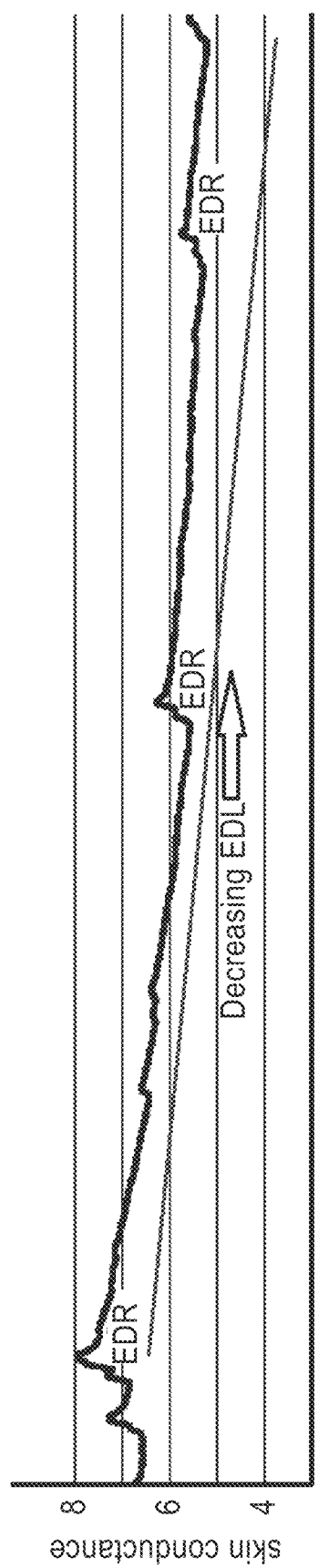
FIG. 13 shows a plot of an example EDA relaxation pattern with a continuously descending EDL baseline and occasional EDR deflections caused by a deeper inhalation.

FIG. 13 shows an example EDA relaxation pattern recorded during a meditation session. The pattern shows a steady decrease in the EDL baseline. In this physiological situation, no sweat is available on the skin for biosensor analysis, so an occasional inhalation EDR in conjunction with the decreasing trend in the EDL can be used to activate the biosensor to do periodic cortisol assays, and to assay for oxytocin—an indicator of parasympathetic nervous system (PNS) activity. Decreased cortisol levels and increased oxytocin levels are healthy indicators of stress reduction.

Figure 14:
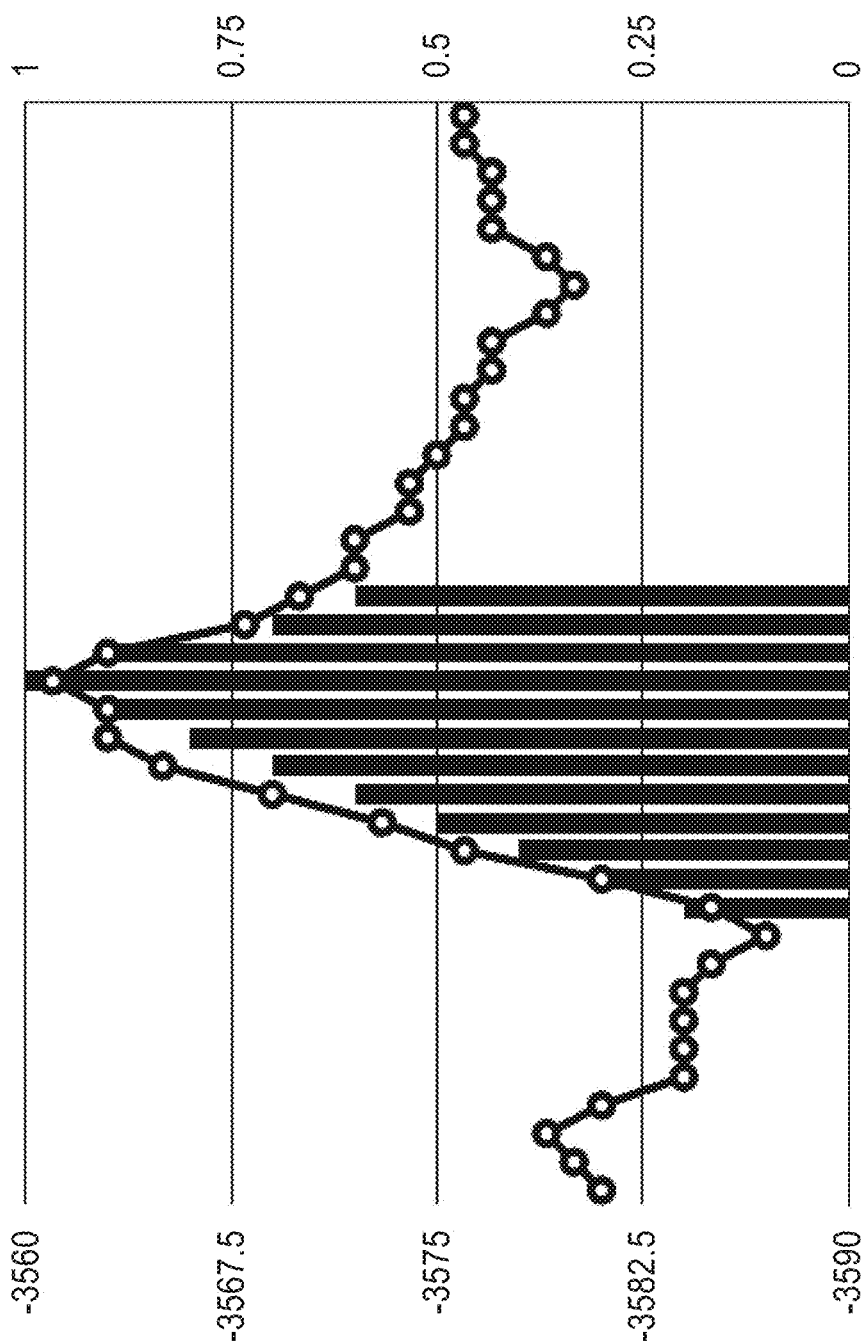
FIG. 14 shows an example data plot of a Machine Learning (ML) network output that has been trained to recognize a single EDR wave.

These types of EDA patterns can be also recognized by a machine learning (ML) algorithm, which can then activate the biosensor assay process. FIG. 14 shows an example data plot of an ML network that has been trained to recognize a single EDR wave. The green bars under the raw data plot show the ML network tracking the area under the wave and will generate a percentage confidence score for an EDR. The results of our ML recognition of individual EDRs indicate that it is possible for ML to recognize more complex EDA patterns, such as shown in FIG. 12 and FIG. 13.

Figure 15:
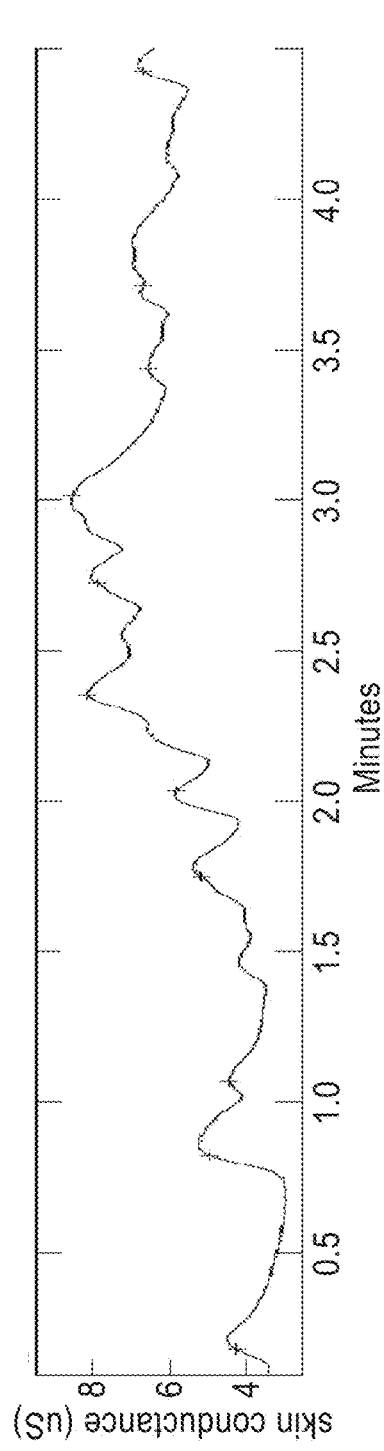
FIG. 15 shows an example output from a peak-picking algorithm in accordance with the present description.

An additional level of signal processing can be implemented that enables more complex EDA patterns to be categorized, and over longer periods of time, as exemplified in Section 3.5. The first stage of the additional processing involves using a peak-picking algorithm to find the EDR wave peaks. The data is first high pass filtered to minimize the low frequency fluctuations, then the peak detection code using a moving average window looks for a change from positive to negative, and then checks that the size of the change against a set threshold. Then the inter-peak interval (IPI) is calculated for each EDR wave. FIG. 15 illustrates the output of a peak picking algorithm for a 4-minute segment of EDA data. The small crosses on the wave form show the time stamped locations of the peaks found by the algorithm.

Figure 16:
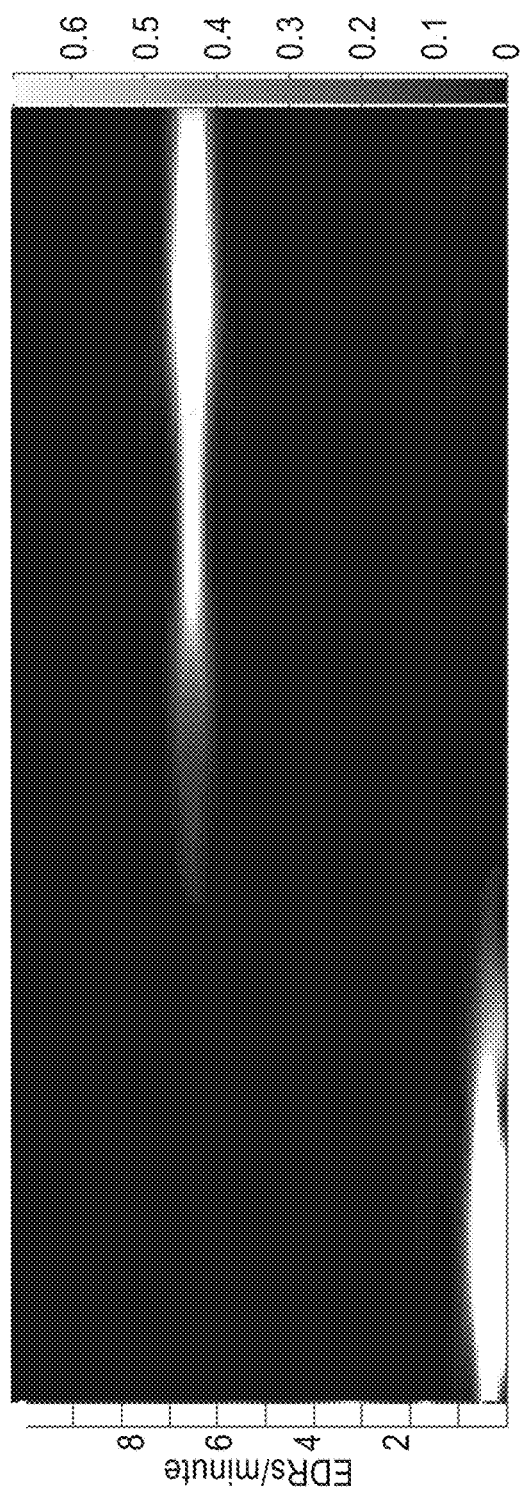
FIG. 16 is a time varying spectrogram showing the output of an FFT calculation that uses a 30 second moving window.

The IPIs can be averaged over a specified time interval and displayed in graphical form along a timeline. Referring to the time varying spectrogram FIG. 16, the IPI data can be used to generate a power spectrum using FFT analysis particularly suited for tracking EDA changes over time as exemplified in FIG. 12 and FIG. 13. The spectrogram of FIG. 16 displays the output of an FFT calculation that uses a 30 second moving window. Frequency is shown on the vertical scale and the power or amplitude of the activation peaks is grey-scale coded (color may also be used)—with lack being the lowest amplitude, grey representing the mid-range, and white showing the greatest amplitude. The spectrogram shown in FIG. 16 corresponds to the EDA plot shown in FIG. 12. In FIG. 12 the EDR rate is around 1 per minute for the first 5 minutes of the data recording. At the 5 minute mark the EDR rate abruptly increases to 6-7 per minute and remains at that rate for the remainder of the recording. The time varying EDR frequencies are actually plotted in FIG. 16.

The data represented in a spectrogram makes ML pattern recognition of EDA data more efficient since the pre-processing yields an array of frequency, intensity, and time values. So rather than analyzing each waveform as shown in FIG. 14, a ML network can analyze longer data sets in order to find larger patterns in user behavior. For example, the patterns may be related to time of day, employment situations, or recreational activities, to name a few. The wearable system can then be programmed to activate the biosensor assay process at specific intervals during the user situation of interest.

3.5. Longer Term Data Recording and Biomarker Tracking

The biometric ring 200 and application software 82a can be used for longer term tracking of user data, and the data trends can indicate chronic physiological states such as the stages of allostatic load.

Existing sources on stress and adaptation to stress use the term "allostatic load" to describe the price the body pays for adapting to different stressors and environmental stimuli. Currently, allostatic load is assessed by occasional measurements of bio-markers in the blood. The test is inconvenient for the user and is performed periodically depending on how often the user goes to a clinic for a blood test (e.g. once per month). In contrast, the biometric ring 200 and EDA sampling method of the present description are able to make assessments of the state of allostatic load by regularly sampling of user cortisol levels. Thus, users have the convenience of a noninvasive assessment done on a continual basis.

Long term stress has recently been shown to cause a host of physiological abnormalities which can be described by the umbrella term "metabolic syndrome". Given the huge numbers of people affected by stress and metabolic syndrome in the US, the ability of the analysis system of the present description to help people monitor and manage their stress levels has huge public health implications.

The biometric ring 200 and EDA sampling method of the present description may be configured to categorize and score the severity of the four types of allostatic load. These four represent different types of physiological adaptation to long term stress: (a) Repeated hits, (b) Prolonged response, (c) Lack of adaptation, and (d) Inadequate response. FIG. 17a through FIG. 17E show example plots of a stress biomarker that illustrate the physiological state of the four allostatic load categories. The EDA triggering method of the present description can display the cortisol levels in the app to produce substantially similar data plots as shown in this figure.

Figure 17A:
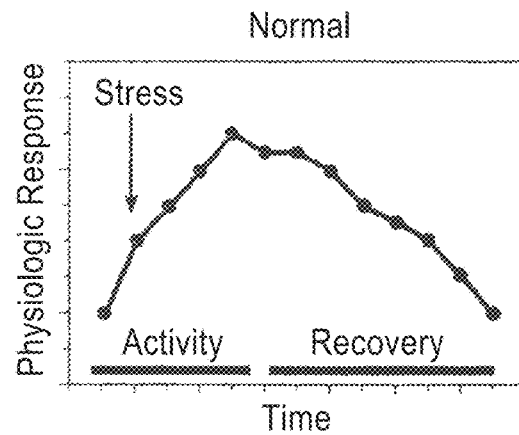
FIG. 17A through FIG. 17E are exemplary plots of a stress biomarker that illustrate the physiological state of normal and four allostatic load categories.
Figure 17B:
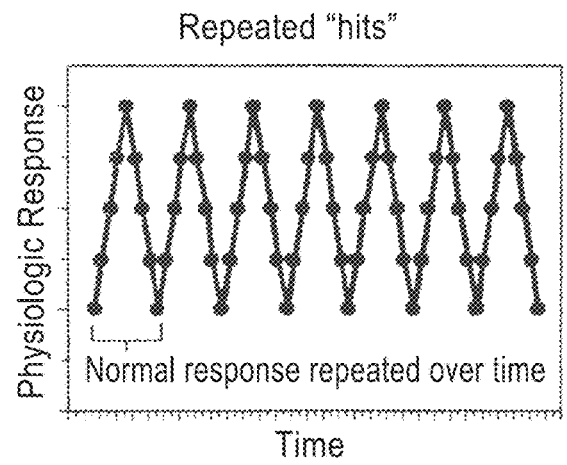

FIG. 17A shows a normal reaction to stress—where there is a rapid increase in SNS activation followed by a gradual decrease back to the baseline. In FIG. 17B, the "repeated hits" category indicates the reaction to continual stressful events of different types. The biometrics show repeated SNS activations and corresponding peaks of cortisol levels, with recoveries that decrease in effectiveness over time. The "repeated hits" plot essentially shows multiple normal reactions but repeated 2 to 3 times per hour over the course of a day. When the data is plotted over the course of a week, the average number of SNS activation epochs per day is 20-30 and is a warning that user is seriously burdening the body with excess stress hormones.

Figure 17C:
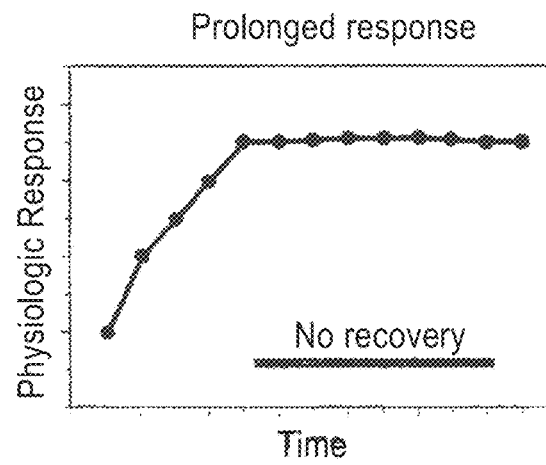

FIG. 17C shows a "prolonged response" if the SNS activation continues for 2-4 hours with no recovery as we see in the case of the normal response. The biometrics of this condition, for instance, show activation in the morning with sustained increase in cortisol levels for most of the day. With sustained high activation levels in the evening, sleep patterns are disrupted. Sleep deprivation compounds the condition the next day.

Figure 17D:
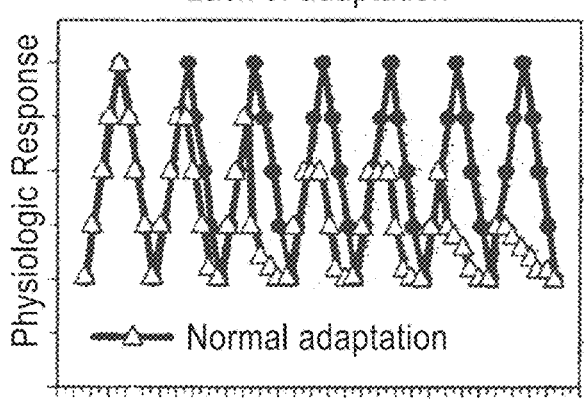

In FIG. 17D, "lack of adaptation" biometrics show repeated strong SNS activations to the same environmental stimuli day after day—that are reported as normal or not stressful by friends or fellow employees. The plot with the blue triangles shows how a normal user would show less and less reaction, e.g. cortisol response, over time. An example case is—if the user is a delivery truck driver and displays these biometrics every time he/she makes a delivery stop during the day, this indicates lack of adaptation and keeps the body in a constant state of over activation that is exhausting for the hormonal homeostatic mechanisms of the SNS.

Figure 17E:
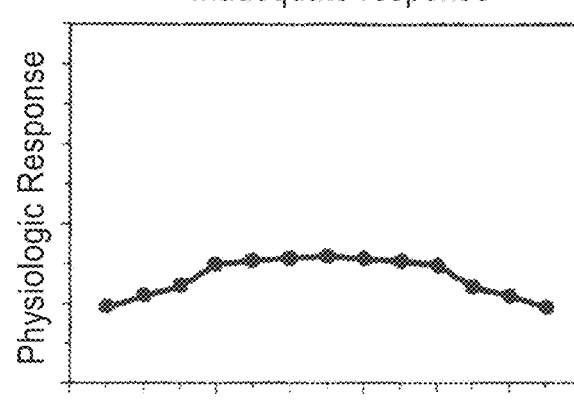

"Inadequate response" biometrics show little or no SNS activations in response to events that friends or co-workers consider stressful. FIG. 17E shows a biometric graph representing very low SNS activation—basically no cortisol stress response. This type of data plot over the course of a work day indicates that the user's normal adrenal hormone response to stress is exhausted. In this condition, other homeostatic mechanisms come into play that lead to auto-immune dysfunction and further damage to the body.

4. Mobile Phone Apps

In the embodiment of the biometric ring 200 shown in FIG. 4, the integrated BLE processor has sufficient internal program memory 66 to perform the EDR amplitude triggering function and then send activation code or signals 50_f_ to the biosensor 202—and then transmit biosensor values 50_e_ and EDA data 50_c_ to the smart phone 78 for display on the app screen via programming 82_a_. This capability also enables a variation on the user experience in that a small LCD or LED display on the ring 200 (not shown) can provide biomarker metrics to the user without the need for data streaming to the smart phone.

EDA pattern recognition software embedded in programming 82_a_ on the smart phone 78 may analyze the data and send biosensor activation code to the ring 200 when pre-programmed pattern matching has occurred. In a current version of ML algorithm training, Apple development tools enable a ML network to use a set of training data and then package the trained algorithm so it will run on the smart phone 78. In this case, once the algorithm can score an EDR wave or a series of EDA events (both EDR and EDL) with high reliability, then the algorithm can run in real-time on the smart phone 78 and display results to the user.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general-purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, hardware processor, computer processor, central processing unit (CPU), and computer are used synonymously to denote a device capable of executing the instructions and communicating with input/output interfaces and/or peripheral devices, and that the terms processor, hardware processor, computer processor, CPU, and computer are intended to encompass single or multiple devices, single core and multicore devices, and variations thereof.

From the description herein, it will be appreciated that that the present disclosure encompasses multiple embodiments which include, but are not limited to, the following:

1. An apparatus for continuous monitoring of sympathetic nervous system SNS activity of a user, comprising: (a) a housing configured for retention on a finger of the user; (b) an electrodermal activity (EDA) sensor disposed within the housing so as to contact a location of the skin of the finger when the housing is retained on the finger, the EDA sensor configured for measuring changes in skin impedance indicative of SNS activation; (c) a biometric sensor disposed within the housing in proximity to the EDA sensor so as to contact at or near said location of the skin of the finger; (d) a processor configured to receive input from the EDA sensor and the biometric sensor; and (e) a non-transitory memory storing instructions executable by the processor; (f) wherein said instructions, when executed by the processor, perform one or more steps comprising: (i) acquiring one or more of electrodermal response (EDR) data and electrodermal level (EDL) data from the EDA sensor; (ii) acquiring biometric sensor data from the biometric sensor data as a function of the EDA sensor; and (ii) assessing the physiological state of the user based on the acquired EDA sensor data and biometric sensor data.

2. The apparatus of method of any preceding or following embodiment: wherein the housing comprises a ring housing having an aperture; wherein EDA sensor and biometric sensor are disposed on a bottom interior surface of the aperture the ring housing to contact the skin on a palmar skin location of the user's finger, the palmar skin location comprising a high density of eccrine sweat glands responsive to SNS activation.

3. The apparatus of method of any preceding or following embodiment, wherein the biometric sensor is configured to assay specified biomarkers from perspiration of the user.

4. The apparatus of method of any preceding or following embodiment: wherein the EDA sensor comprises a pair of spaced-apart electrodes; and wherein the biometric sensor is disposed between the spaced-apart electrodes of the EDA sensor.

5. The apparatus of method of any preceding or following embodiment, wherein said instructions when executed by the processor further perform one or more steps comprising: initiating acquisition of the biomarker assay data from the biometric sensor as a function of the acquired EDA sensor data.

6. The apparatus of method of any preceding or following embodiment, wherein said instructions when executed by the processor further perform one or more steps comprising: identifying of one or more EDR peaks within the acquired EDA sensor data; and initiating acquisition of the biomarker assay data from the biometric sensor as a function of the identified EDR peaks.

7. The apparatus of method of any preceding or following embodiment, wherein said instructions when executed by the processor further perform one or more steps comprising: combining and correlating the EDA sensor data with the assayed biomarkers for use in assessing the physiological state.

8. The apparatus of method of any preceding or following embodiment, wherein the biometric sensor comprises a photoplethysmograph (PPG) sensor for receiving analog pulse rate data from the user.

9. The apparatus of method of any preceding or following embodiment, further comprising wireless circuitry coupled to the processor, and wherein said instructions when executed by the processor further perform one or more steps comprising: transmitting acquired EDA sensor data and biometric sensor data to an external device; and performing one more of the steps on the external device for display to the user.

10. The apparatus of method of any preceding or following embodiment, wherein the biometric sensor forms a field effect transistor such that target molecules from the user interact with a surface of the biometric sensor to modulate the current output of the biometric sensor.

11. A method for continuous monitoring of sympathetic nervous system SNS activity of a user, comprising: retaining a housing on a finger of the user, the housing comprising an electrodermal activity (EDA) sensor configured for measuring changes in skin impedance indicative of SNS activation and a biometric sensor configured to assay specified biomarkers from perspiration of the user; coupling the EDA sensor and biometric sensor to a location of the skin of the finger when the housing is retained on the finger, the EDA sensor; acquiring one or more of electrodermal response (EDR) data and electrodermal level (EDL) data from the EDA sensor; acquiring biometric sensor data from the biometric sensor data as a function of the EDA sensor; and assessing the physiological state of the user based on the acquired EDA sensor data and biometric sensor data.

12. The apparatus of method of any preceding or following embodiment, wherein the housing comprises a ring housing having an aperture, the EDA sensor and biometric sensor being disposed on a bottom interior surface of the aperture the ring housing, wherein coupling the EDA sensor and biometric sensor to a location of the skin comprises: contacting the skin on a palmar skin location of the user's finger, the palmar skin location comprising a high density of eccrine sweat glands responsive to SNS activation.

13. The apparatus of method of any preceding or following embodiment: wherein the EDA sensor comprises a pair of spaced-apart electrodes; and wherein the biometric sensor is disposed between the spaced-apart electrodes of the EDA sensor to acquire biometric data at the location.

14. The apparatus of method of any preceding or following embodiment, wherein acquiring biometric sensor data comprises initiating acquisition of the biomarker assay data from the biometric sensor as a function of the acquired EDA sensor data.

15. The apparatus of method of any preceding or following embodiment, wherein initiating acquisition of the biomarker assay data comprises: identifying of one or more EDR peaks within the acquired EDA sensor data; and initiating acquisition of the biomarker assay data from the biometric sensor as a function of the identified EDR peaks.

16. The apparatus of method of any preceding or following embodiment, further comprising: combining and correlating the EDA sensor data with the assayed biomarkers prior to assessing the physiological state.

17. The apparatus of method of any preceding or following embodiment, wherein the biometric sensor comprises a photoplethysmograph (PPG) sensor, the method further comprising: receiving analog pulse rate data from the user for use in assessing the physiological state.

18. The apparatus of method of any preceding or following embodiment, further comprising: transmitting acquired EDA sensor data and biometric sensor data to an external device; and assessing the physiological state on the external device for display to the user.

19. The apparatus of method of any preceding or following embodiment, further comprising: controlling operation of EDA sensor and biometric sensor; collecting the EDA sensor data and biometric sensor data; analyzing the collected sensor data; and displaying the collected sensor data from the external device.

20. The apparatus of method of any preceding or following embodiment, wherein coupling the EDA sensor and biometric sensor to a location of the skin further comprises: forming a field effect transistor with the biometric sensor and the skin; and modulating a current output of the biometric sensor via interaction of target molecules from the user with a surface of the biometric sensor.

21. An apparatus for continuous monitoring of SNS activity of a user, comprising: (a) an EDA sensor configured to be positioned adjacent the user's skin to allow for acquisition of both electrodermal response (EDR) and electrodermal level (EDL) data from the user; (b) a biosensor in proximity to the EDA sensor, the biomarker configured to assay specified biomarkers from perspiration of the user; (c) a processor configured to receive input from the EDA sensor and the biosensor; (d) a non-transitory memory storing instructions executable by the processor; (e) wherein said instructions, when executed by the processor, perform one or more steps comprising: (i) combining and correlating the EDA sensor data with the biosensor data; and (ii) assessing the physiological state of the user based on the correlated EDA sensor and biosensor data.

22. The apparatus or method of any preceding or subsequent embodiments, wherein said instructions when executed by the processor further perform one or more steps comprising: initiating acquisition of the biomarker assay data from the biosensor upon identification of one or more EDR peaks.

23. The apparatus or method of any preceding or subsequent embodiments, further comprising: wireless circuitry for transmission of the EDA sensor data with the biosensor data to an external device.

24. The apparatus or method of any preceding or subsequent embodiments, wherein the apparatus is disposed in a wearable ring to allow a user to wear the ring for extended periods of time for long-term biometric data collection.

25. A method of monitoring chemical biomarkers and accompanying SNS activity in real life situations using the device in any of the preceding embodiments.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for continuous monitoring of sympathetic nervous system SNS activity of a user, comprising:
   (a) a housing configured for retention on a finger of the user;
   (b) an electrodermal activity (EDA) sensor disposed within the housing so as to contact a location of the skin of the finger when the housing is retained on the finger, the EDA sensor configured for measuring changes in skin impedance indicative of SNS activation;
   (c) a biometric sensor disposed within the housing in proximity to the EDA sensor so as to contact at or near said location of the skin of the finger;
   (d) a processor configured to receive input from the EDA sensor and the biometric sensor; and
   (e) a non-transitory memory storing instructions executable by the processor;
   (f) wherein said instructions, when executed by the processor, perform one or more steps comprising:
     (i) acquiring one or more of electrodermal response (EDR) data and electrodermal level (EDL) data from the EDA sensor;
     (ii) acquiring biometric sensor data relating to one or more chemicals within the skin from the biometric sensor data as a function of the EDA sensor;
     (iii) assessing the physiological state of the user based on the acquired EDA sensor data and biometric sensor data; and
     (iv) initiating acquisition of the biomarker assay data from the biometric sensor as a function of the acquired EDA sensor data;

(g) wherein the housing comprises a ring housing having an aperture;
(h) wherein the EDA sensor and the biometric sensor are disposed on a bottom interior surface of the aperture the ring housing to contact the skin on a palmar skin location of the user's finger, the palmar skin location comprising a high density of eccrine sweat glands responsive to SNS activation; and
(i) wherein the biometric sensor is configured to assay specified biomarkers from perspiration of the user.

2. The apparatus of claim 1:
wherein the EDA sensor comprises a pair of spaced-apart electrodes; and
wherein the biometric sensor is disposed between the spaced-apart electrodes of the EDA sensor.

3. The apparatus of claim 1, wherein said instructions when executed by the processor further perform one or more steps comprising:
identifying of one or more EDR peaks within the acquired EDA sensor data; and
initiating acquisition of the biomarker assay data from the biometric sensor as a function of the identified EDR peaks.

4. The apparatus of claim 1, wherein said instructions when executed by the processor further perform one or more steps comprising:
combining and correlating the EDA sensor data with the assayed biomarkers for use in assessing the physiological state.

5. The apparatus of claim 1, further comprising wireless circuitry coupled to the processor, and wherein said instructions when executed by the processor further perform one or more steps comprising:
transmitting acquired EDA sensor data and biometric sensor data to an external device; and
performing one more of the steps on the external device for display to the user.

6. The apparatus of claim 1, wherein the biometric sensor forms a field effect transistor such that target molecules from the user interact with a surface of the biometric sensor to modulate the current output of the biometric sensor.

7. A method for continuous monitoring of sympathetic nervous system SNS activity of a user, comprising:
retaining a housing on a finger of the user, the housing comprising an electrodermal activity (EDA) sensor configured for measuring changes in skin impedance indicative of SNS activation and a biometric sensor configured to assay specified biomarkers from perspiration of the user;
coupling the EDA sensor and biometric sensor to a location of the skin of the finger when the housing is retained on the finger, the EDA sensor;
acquiring one or more of electrodermal response (EDR) data and electrodermal level (EDL) data from the EDA sensor;
acquiring biometric sensor data relating to one or more chemicals within the skin from the biometric sensor data as a function of the EDA sensor; and
assessing the physiological state of the user based on the acquired EDA sensor data and biometric sensor data;
wherein the housing comprises a ring housing having an aperture, the EDA sensor and biometric sensor being disposed on a bottom interior surface of the aperture the ring housing;
wherein coupling the EDA sensor and biometric sensor to a location of the skin comprises contacting the skin on a palmar skin location of the user's finger, the palmar skin location comprising a high density of eccrine sweat glands responsive to SNS activation; and
wherein acquiring biometric sensor data comprises initiating acquisition of the biomarker assay data from the biometric sensor as a function of the acquired EDA sensor data.

8. The method of claim 7:
wherein the EDA sensor comprises a pair of spaced-apart electrodes; and
wherein the biometric sensor is disposed between the spaced-apart electrodes of the EDA sensor to acquire biometric data at the location.

9. The method of claim 7, wherein initiating acquisition of the biomarker assay data comprises:
identifying of one or more EDR peaks within the acquired EDA sensor data; and
initiating acquisition of the biomarker assay data from the biometric sensor as a function of the identified EDR peaks.

10. The method of claim 7, further comprising:
combining and correlating the EDA sensor data with the assayed biomarkers prior to assessing the physiological state.

11. The method of claim 7, further comprising:
transmitting acquired EDA sensor data and biometric sensor data to an external device; and
assessing the physiological state on the external device for display to the user.

12. The method of claim 11, further comprising:
controlling operation of EDA sensor and biometric sensor;
collecting the EDA sensor data and biometric sensor data;
analyzing the collected sensor data; and
displaying the collected sensor data from the external device.

13. The method of claim 7, wherein coupling the EDA sensor and biometric sensor to a location of the skin further comprises:
forming a field effect transistor with the biometric sensor and the skin; and
modulating a current output of the biometric sensor via interaction of target molecules from the user with a surface of the biometric sensor.

* * * * *